United States Patent
Liprie

(12) 
(10) Patent No.: US 6,635,008 B1
(45) Date of Patent: Oct. 21, 2003

(54) SYSTEM AND METHOD FOR DELIVERING A MEDICAL TREATMENT TO A TREATMENT SITE

(75) Inventor: Samuel F. Liprie, Lake Charles, LA (US)

(73) Assignee: Interventional Therapies LLC, Westport, CT (US)

( * ) Notice: Subject to any disclaimer, the term of this patent is extended or adjusted under 35 U.S.C. 154(b) by 609 days.

(21) Appl. No.: 09/325,944

(22) Filed: Jun. 4, 1999

Related U.S. Application Data

(63) Continuation of application No. 08/814,213, filed on Mar. 11, 1997, now abandoned.

(51) Int. Cl.$^7$ ................................................ A61N 5/00
(52) U.S. Cl. ................ 600/3; 600/1; 600/7; 250/497.1
(58) Field of Search ....................... 600/1, 3, 7, 6; 250/497.1, 496.1

(56) References Cited

U.S. PATENT DOCUMENTS

| | | |
|---|---|---|
| 1,753,287 A | 4/1930 | Failla |
| 1,953,915 A | 4/1934 | Burgett et al. |
| 1,954,868 A | 4/1934 | Failla et al. |
| 2,546,761 A | 3/1951 | Loftus |
| 2,904,272 A | 9/1959 | Barrett |
| 3,669,093 A | 6/1972 | Sauerwein et al. |
| 3,848,137 A | 11/1974 | Ellis |
| 3,861,380 A | 1/1975 | Chassagne et al. |
| 3,866,050 A | 2/1975 | Whitfield |
| 4,096,862 A | 6/1978 | DeLuca |
| 4,150,298 A | 4/1979 | Brault et al. |
| 4,220,864 A | 9/1980 | Sauerwein et al. |
| 4,574,196 A | 3/1986 | Kampf |
| 4,584,991 A | 4/1986 | Tokita et al. |
| 4,631,415 A | 12/1986 | Sauerwein et al. |
| 4,692,628 A | 9/1987 | Sauerwein et al. |
| 4,733,653 A | 3/1988 | Leung et al. |

(List continued on next page.)

FOREIGN PATENT DOCUMENTS

| | | |
|---|---|---|
| DE | 3442762 | 6/1986 |
| DE | 3643902 | 6/1988 |
| EP | 0012004 | 6/1980 |
| EP | 0152124 | 8/1985 |
| EP | 0158630 | 10/1985 |
| EP | 0254351 | 1/1988 |
| EP | 0366214 | 5/1990 |
| GB | 0857992 | 1/1961 |

(List continued on next page.)

OTHER PUBLICATIONS

Nucletron ® Brochure; Remote Afterloading System; Feb. 1988.
Nucletron ® Brochure; Remote Afterloading System.
Afterloading systems and Instiial Applications; Principals and Practice of Radiation Oncology.

*Primary Examiner*—Rosiland S. Kearney
(74) *Attorney, Agent, or Firm*—Cantor Colburn LLP

(57) ABSTRACT

A system is provided for delivering a medical treatment to a treatment site in a vessel or other conduit in a mammalian body, including an afterloader including a housing, a drive member, and a conduit having a first end operatively associated with an output portion of the drive member, and a connector disposed at a second end, the connector defining a first mating surface, an elongated transport tube having a proximal end defining a second mating surface, the first and second mating surfaces being complementarily configured and dimensioned such that a continuous passageway is formed between the conduit and the elongated transport tube, and a locking member positionable within a channel formed adjacent either the first or second mating surfaces and being configured and dimensioned such that upon insertion of the locking member in the channel the first and second mating surfaces are securely mated.

21 Claims, 3 Drawing Sheets

U.S. PATENT DOCUMENTS

| | | |
|---|---|---|
| 4,851,694 A | 7/1989 | Rague et al. |
| 4,881,937 A | 11/1989 | van't Hooft et al. |
| 4,881,938 A | 11/1989 | van't Hooft |
| 4,897,076 A | 1/1990 | Puthawala et al. |
| 4,969,863 A | 11/1990 | van't Hooft et al. |
| 5,030,194 A | 7/1991 | van't Hooft |
| 5,084,001 A | 1/1992 | van't Hooft et al. |
| 5,092,834 A | 3/1992 | Bradshaw et al. |
| 5,103,395 A | 4/1992 | Spako et al. |
| 5,120,973 A | 6/1992 | Rohe et al. |
| 5,139,473 A | 8/1992 | Bradshaw et al. |
| 5,147,282 A | 9/1992 | Kan |
| 5,199,939 A | 4/1993 | Dake et al. |
| 5,213,561 A | 5/1993 | Weinstein et al. |
| 5,295,959 A | 3/1994 | Gurbel et al. |
| 5,344,383 A | 9/1994 | Liping |
| 5,503,041 A | 4/1996 | van't Hooft |
| 5,503,614 A | 4/1996 | Liprie |
| 5,556,389 A | 9/1996 | Liprie |
| 5,605,530 A | 2/1997 | Fischell et al. |

FOREIGN PATENT DOCUMENTS

| | | |
|---|---|---|
| GB | 1295559 | 1/1984 |
| GB | 0271844 | 9/1989 |
| SU | 0279814 | 7/1975 |
| SU | 0649412 | 2/1979 |
| WO | 9200776 | 1/1992 |

SYSTEM AND METHOD FOR DELIVERING A MEDICAL TREATMENT TO A TREATMENT SITE

This is a continuation of application Ser. No. 08/814,213, filed on Mar. 11, 1997 and entitled, "System and Method For Delivering A Medical Treatment To A Treatment Site" now abandoned, the entire disclosure of which is incorporated by reference herein.

BACKGROUND

1. Technical Field

The present disclosure relates to remote afterloading devices used to position radioactive treatment source wires inside patients afflicted with cancer or other diseases, and more particularly to a system and method for delivering a medical treatment to a treatment site of such patients.

2. Background of Related Art

Radiation is used to treat cancer and other diseases of the body. Brachytherapy, is a general term for the radiation treatment of cancer at close distances inside the body. During brachytherapy, a radioactive source or sources are positioned in the area needing treatment. Depending on the type of therapy, the radioactive sources are placed permanently inside the body during surgery, or transport tubes (treatment catheters) are placed in the body which are later temporarily loaded with radioactive sources. This temporary afterloading of radioactive material either involves a human handling the radioactive material and receiving radiation exposure, or a machine called a "remote afterloader" that will load and unload the radioactive material into and from the transport tubes. Such remote afterloaders are operated by an individual from a remote location so that the individual will not receive any radiation exposure.

Existing remote a afterloaders are generally used in the cancer field to accurately advance and retract a flexible drive member containing a radioactive source over a specified distance for a specified time period. A remote afterloader generally consists of a flexible simulation drive member, a flexible drive member containing a radioactive element, controllers and drive mechanisms to operate both types of flexible members, a shielding safe for the radioactive element, an internal timer, and an exit port attached to a rotating wheel that allows multiple transport tubes (previously placed into the patient) to be attached to device at the same time.

It is known to use a simulation member for checking the patency of the transport tube without subjecting the patient to undue radiation exposure. After the patency is confirmed, the afterloader sends out the radioactive source. Upon completion of treatment in a first transport tube, the afterloader retracts the source into the shielding safe inside the afterloader, a wheel turns and aligns a slot containing a second transport tube to an exit port. The remote afterloader then repeats its function sending and retracting the simulation member and radioactive source through this second tube. The procedure is repeated until the function is carried out through all the specified transport tubes. Existing remote afterloaders use a fixed, short length radioactive source and multi-step this source many times inside each transport tube to cover the diseased area.

Currently available remote afterloaders require the following complicated procedures before any treatment can take place:

Initially, by hand, physical measurements must be made of each transport tube after it has been positioned inside the body using a simulation member, fluoroscopy, and a calibrated ruler. These measurements must accurately relate the physical distance the radioactive source needs to travel from the distal end of each tube to the inside of each transport tube to treat the disease inside the body.

Secondly, two 90 degree X-Rays showing all the transport tubes inside the body must be made and digitized into a treatment planning computer. The physical measurements taken prior to the X-rays, must be matched up with each digitized transport tube in the treatment planning computer and the physical length measurements along with other treatment data must be entered for each transport tube.

The computer then compiles all the data and a treatment plan is formed and stored on a magnetic computer disk. This computer disk containing the treatment plan is then entered into a treatment computer that programs and operates the remote after-loader. Finally, the treatment takes place.

In most cases, the above setup steps take thirty minutes or more. Existing remote afterloaders were primarily designed for the treatment of cancer but can be used in other treatments of diseases. There are critical factors that will not allow the previously available remote afterloaders to be used in the treatment of certain types of diseases. One main limiting factor is the long setup time required for treatment. In treatments where time is of the essence, such as in the treatment of heart patients, a long setup time could be unacceptable. The present disclosure allows a specially designed remote afterloader to perform its duty in a much shorter time period, eliminating many of the time consuming steps.

Other limiting factors of previous treatment afterloaders are the physical size and amount of equipment necessary to operate a remote afterloader. In many treatment facilities there is not enough room for the amount and size of equipment. Lack of certain safety features (for example, an indirect but not a direct transport tube sensing device to ensure that the transport tube is properly connected to the afterloader, human error when measuring and translating treatment distance, no control of the speed in which the drive members move, no means to fine tune the position of the drive members once they reach their target area) along with the lack of other safety features make the previously available remote afterloaders limited in use and effectiveness.

Various techniques have been developed to treat many different conduits in the body when these conduits have become reduced in size due to the existence of a stenosis or have been completely occluded. These techniques include introducing a deflated balloon catheter to the site of an occlusion or constriction, such as a stenosis, inflating the balloon one or more times to reduce the size of the stenosis, deflating the balloon and then removing the balloon catheter from the treatment site.

With respect to the vascular pathways, angioplasty is used to open an artery or blood vessel in the region where the stenosis or the occlusion has occurred. A typical angioplasty procedure consists of making a small incision through the body and into a blood vessel and then maneuvering a guide wire through the vascular system to a point beyond the stenosis or occlusion. A hollow catheter with a declarable balloon near its distal end is threaded over the guide wire and advanced to the point of stenosis or occlusion. The balloon is then inflated and deflated several times to widen the constricted area, and is then withdrawn from the body.

Unfortunately, although the angioplasty procedure does markedly reduce the area of stenosis or occlusion, many patients exhibit a reoccurrence of the stenosis within a few months of the original procedure.

Although the original stenosis occurs by means of the build up of plaque over a relatively long period of time, experimentation has led many to believe that the reoccurrence of the stenosis after the original angioplasty procedure is unrelated to the cause of the original stenosis. It is believed that the inflation of the balloon catheter used in the angioplasty procedure or the placement of a sent in the area of the stenosis causes irritation to the blood vessel. This irritation produces a mechanism of action called hyperplasia, inducing the inner layer of the blood vessel cells to rapidly reproduce, thereby causing restenosis. It has been proposed that if the blood vessel is irradiated at the point of the stenosis with a radioactive dose, the mechanism that causes hyperplasia would be destroyed without harming the blood vessel itself.

During this procedure, it is important to precisely control the amount of radiation which is directed to the blood vessel wall, since too much radiation could actually induce hyperplasia as well as destroying a portion of the blood vessel, making it possible for an aneurism or rupture to occur.

U.S. Pat. No. 5,213,561 issued to Weinstein et al and U.S. Pat. No. 5,199,939 issued to Dake et al, as well as PCT Application PCT/US92/07447 to Shefer et al, describe various methods and apparatus for introducing radiation to the site of a stenosis to endeavor to prevent rustiness.

The Weinstein et al patent describes a method and apparatus for preventing rustiness after angioplasty. A balloon catheter transported by a conventional guide wire is delivered to the location of the stenosis. Particles or crystals of radioactive material are embedded or mounted on a tube provided inside the balloon catheter. A retractable radiation shielding sleeve is slidable along the tube to cover the source of radioactive material. Upon completion of the angioplasty, the shielding sleeve is retracted and the area of the stenosis is irradiated. Although this apparatus does introduce radiation to the point of the stenosis, the retractable shielding surrounding the source of radioactive material makes this catheter bulky and unwieldy to use. In this regard, it is very doubtful that a catheter system this bulky would fit into the smaller branches or vessels of the heart. It is also doubtful that a catheter this bulky and stiff could be maneuvered through the tighter bends and turns in many of the vessels.

An additional embodiment of the Weinstein et al. patent illustrates a sent which is made of or coated with a radioactive material such as iridium 192. Since the radioactive material is provided on the outer surface of the sent, it is very difficult to precisely administer the proper dosage of radiation to prevent hyperplasia without administering a level of radiation which would actually induce hyperplasia or other deleterious effects to the blood vessel.

The Shefer PCT application illustrates a method and apparatus for restenosis treatment by applying a radioactive dose to the stenosed region after reduction of the region by angioplasty or other means. An angioplasty balloon is expanded in the vicinity of a lesion site and radioactive elements provided on the exterior surface of the balloon are forced into contact with the region. Therefore, similar to the Weinstein et al. patent, the presence of the radioactive material on the exterior of the catheter would make it very difficult to apply the precise amount of radiation to the region of interest. Additionally, both the Shefer PCT application and the Weinstein patent describe balloon catheters which do not allow the blood within the vessel to flow during inflation of the balloon.

Although there have been some attempts to construct a dilatation balloon allowing for some perfusion of bodily fluids during the inflation phase of the dilatation, the perfusion is greatly diminished by the overall size of the inflated balloon. Dilatation balloons must be able to hold a great amount of pressure (up to 16 atmospheres) and must also be able to inflate to large overall diameters to open the stenosis areas inside the bodily conduits or narrow tortuous passageways. Both of these requirements lead to large, bulky dilatation balloons that encompass most, if not all, of the area inside the stenosed vessel leading to large blockages of bodily fluids and thus allowing for little, if any perfusion.

Examples of these types of balloons are described in U.S. Pat. Nos. 5,295,959, issued to Gurbel et al and 5,308,356, issued to Blackshear, Jr. et al. Both of these patents describe a passive perfusion dilatation catheter having a series of non-longitudinal lobes. As particularly illustrated in the Blackshear, Jr. et al patent, virtually the entire interior of the bodily conduit is blocked when the dilatation balloon is inflated, thereby preventing the flow of bodily fluids around the treatment site. Additionally, due to the particular structure of the balloons utilized, neither the Gurbel et al. nor the Blackshear, Jr. et al. balloon can be used to precisely position the catheter within the bodily conduit at the site of treatment.

Attempts to utilize these types of dilatation balloons as a positioning balloon or treating the patient with radioactive materials would greatly compromise the patient during implementation of the treatment due to the diminished flow of bodily fluids or, in some cases, the complete blockage of bodily fluids. Any compromises to the dilatation balloon to achieve a greater flow rate would greatly decrease the effectiveness of the balloon on the stenosed area.

SUMMARY

The present disclosure addresses the deficiencies of previous devices by treating the location of a stenosis in a blood vessel, or other hollow conduit or narrow tortuous passageway in the body by utilizing a dilatation balloon (or series of balloons) in conjunction with a stand-off balloon (or series of balloons), both of which are attached near distal end of a catheter. A radiopaque elongated, flexible guidewire is inserted into the body through a small incision and is then introduced into a blood vessel or similar conduit or passageway. Once in place, a catheter including the aforementioned dilatation balloon or balloons as well as one or more stand-off balloons would be maneuvered to the location of treatment.

The dilatation balloon or balloons is inflated and deflated one or more times to reduce the size of the stenosis. At this point, the stand-off balloon or balloons would be inflated. Since the stand-off balloons inflate symmetrically and are long with thin widths, they serve to position the treatment lumen of the catheter inside the prior stenosised area while allowing for maximum bodily perfusion. A radioactive source or sources is advanced into position through the treatment lumen of the catheter to the site of the original stenosis. With the stand-off balloon or balloons inflated, the catheter and the radioactive source or sources are correctly positioned within the bodily conduit or passageway to administer the precise dose to the original area of the stenosis. After a predetermined period of time has elapsed, the stand-off balloon or balloons are deflated and the radioactive source as well as the catheter and a guidewire are removed from the bodily conduit or passageway.

A normal angioplasty catheter including the catheter utilizing both dilatation as well as stand-off balloons are provided in a sterile ,package and is used entirely in a sterile environment to prevent contamination from being introduced into the patient's body. The treatment channel or lumen of the aforementioned catheter is positioned within the catheter and contains an inner, closed channel. A radioactive source or sources is maneuvered from an afterloader through this channel until it nears the closed end to deliver therapy within the patient's body.

The above-noted and other deficiencies of prior afterloaders are addressed by the present disclosure which is directed to a treatment catheter allowing a radioactive source or sources to be maneuvered from an afterloader in a non-sterile environment into a sterile environment without the occurrence of contamination. If a catheter employing both stand-off as well as dilatation balloons are placed into the patient's body, it is important that the portion of the treatment lumen from the balloon inflation channel or channels to the distal end of the catheter provided within the patient's body, must all be contained within a working sterile environment. It is noted that for purposes of explanation, the present disclosure is described with respect to a catheter employing both dilatation as well as stand-off balloons. However, as can be appreciated by practitioners in the medical art, it is not necessary to utilize this type of catheter to practice the teachings of the present disclosure.

It is not always possible to place a non-sterile radioactive source or sources into the treatment lumen of a catheter if the lumen is similar in length to the inflation lumen or lumens for inflating and discharging the dilatation or stand-off balloons without breaking the sterile field. Therefore, in order to maneuver this non-sterile radioactive source or sources through the treatment channel or lumen without breaking the sterile environment, a transport channel, or tube, protruding from the proximal end of the treatment channel of the catheter must be employed. This extra-long transport/treatment channel can be appreciably longer than the inflation lumen or lumens. This design allows an individual or an afterloading device located in an area outside the sterile field to maneuver the non-sterile source or sources through the treatment lumen to the treatment site, without breaking the surrounding sterile field.

There are two methods in which a radioactive source or sources can be loaded into the opening of the transport tube. One method is to physically load the source or sources by hand or by the use of forceps or other types of manipulators into the treatment channel. The second method is to load the source or sources by use of the remote afterloader. In order to accomplish this loading task, a specially designed hub provided on the proximal end of the transport tube must be utilized. This hub design contains a tapered or funnel opening to allow the radioactive source or sources to easily enter the proximal end of the transport tube of the catheter.

Therefore, the present disclosure features an extra long length treatment tube protruding from the proximal end of the catheter in conjunction with dilatation and/or stand-off balloons to allow a radioactive source or sources to be maneuvered from a non-sterile environment into the sterile environment of the patient's body. The present disclosure further features a specially designed hub to assure the correct fit and connection of the treatment lumen to the afterloading device. This specially designed hub also directly communicates with the afterloading device after it is locked in place to insure that the connection between the treatment catheter and the afterloader is complete.

BRIEF DESCRIPTION OF THE DRAWINGS

The above and other objects, features and advantages of the present disclosure will become apparent in the following description and the appended claims taken in conjunction with the accompanying drawings in which:

DETAILED DESCRIPTION OF PREFERRED EMBODIMENTS

Figure 1A:
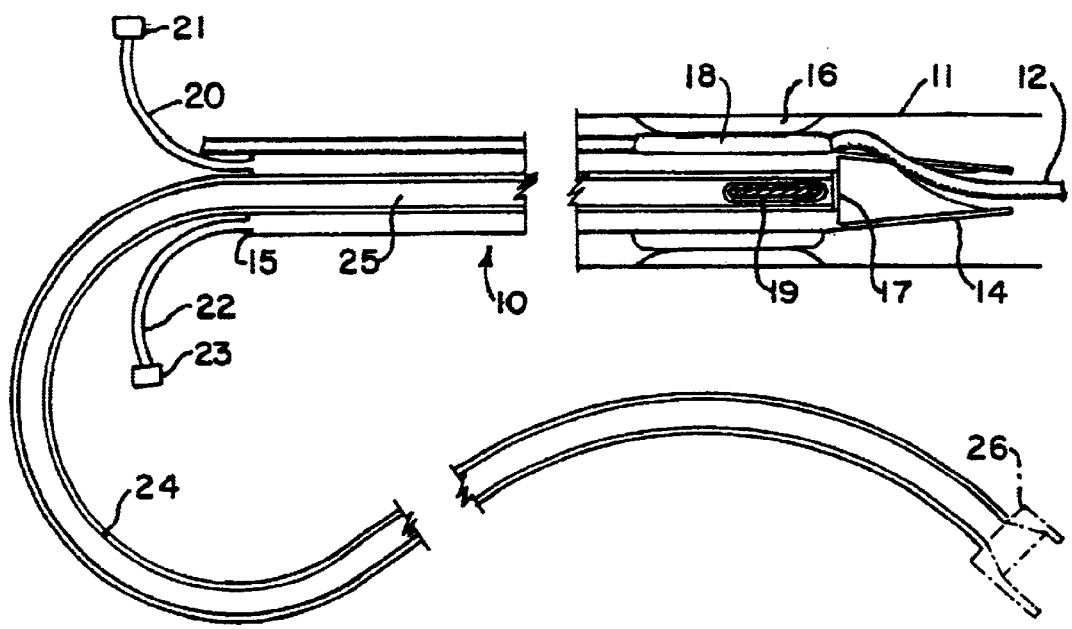
FIG. 1A is a longitudinal view of a catheter showing a long extruded treatment channel projecting from the body of the catheter.

Although the present disclosure can be used to treat blockages, occlusions, or constrictions in many body conduits as well as narrow tortuous passageways, for the ease of explanation, the present disclosure will be discussed with respect to a stenosis provided in a blood vessel. Additionally, also for ease of explanation, the same reference numerals will be used for like features.

Referring to FIG. 1A a catheter 10 includes a tapered distal end 14 which is directed past the treatment site including an area of stenosis 16 within a blood vessel 11. The catheter 10 is manufactured in such a manner that it is relatively flexible and elongated and is provided with a large hollow treatment lumen 25 running from the catheter distal end 14 to a proximal end 15.

An elongated flexible guidewire 12 is maneuvered to the treatment site to treat the stenosis. Guidewire 12 passes through a narrow guidewire lumen that exits out the side of catheter 10 so guidewire 12 runs along the outside surface of catheter 10. Alternatively, the guidewire 12 could pass through a narrow guidewire lumen provided adjacent to one of the surfaces of a treatment lumen 25.

The catheter 10 is provided with one or more dilatation balloons 18 affixed to the exterior surface of the catheter 10. These dilatation balloons 18 are provided close to a tapered end 14 of catheter 10. A radiopaque solid plug 17 or similar device is provided in the distal end of the catheter at the point where the catheter begins to taper. Plug 17 ensures that a radiation source 19 which is maneuvered to the treatment site through the treatment lumen 25 remains within the interior of the catheter 10. Furthermore, plug 17 ensures that contamination or germs potentially included within the treatment lumen 25 do not mix with bodily fluids provided within the blood vessel 11.

Radiation source 19 may be a radiation "seed" or seeds which are transported to the treatment site and left there. Alternatively, a flexible radiation source wire may be utilized. Such source wires typically contain a radiation source disposed within a hollow lumen formed at the distal end of an elongated wire. Examples of such source wires are disclosed in applicant's U.S. Pat. Nos. 5,503,614 issued on Apr. 2, 1996 and 5,556,389 issued on Sep. 17, 1996, the entire contents of these patents are hereby incorporated by reference. Typical of the radiation sources which may be utilized, are cesium 137, cobalt 60, iodine 125, iodine 131, cobalt 57, iridium 192, gold 198, palladium 103, strontium 89, strontium 90, phosphate 32 or yttrium 90.

Figure 1B:
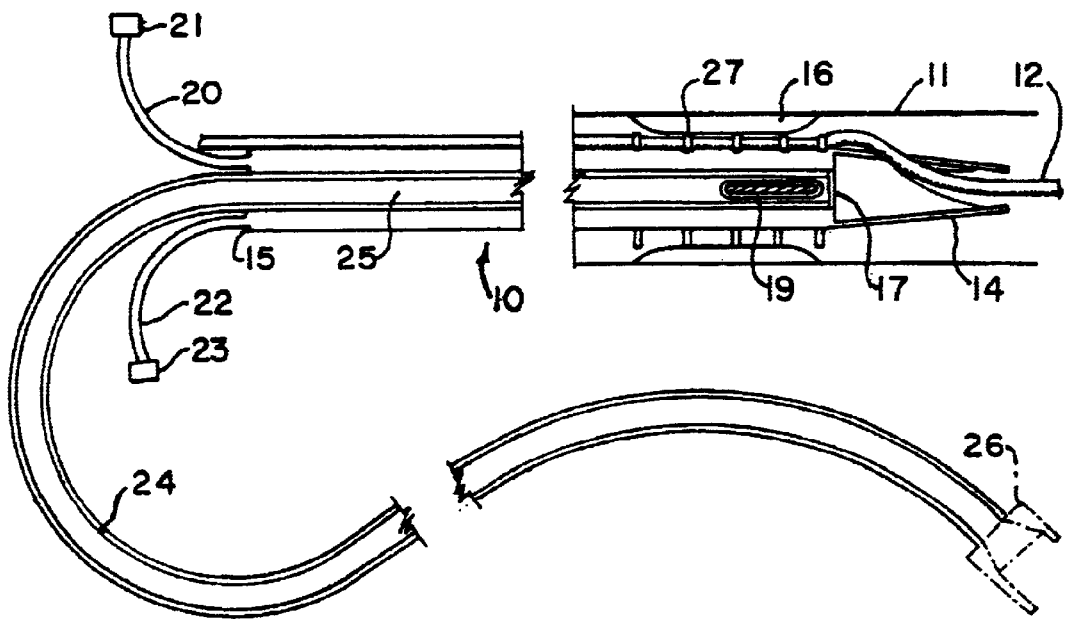
FIG. 1B is a view similar to FIG. 1A, which illustrates a stand-off balloon arrangement according to the present disclosure.

The dilatation balloon 18 is inflated and deflated utilizing a lumen 20 connected to a balloon inflation port 21. Referring to FIG. 1B, a standoff balloon 27 is shown which may be provided to keep the catheter 10 spaced at least a predetermined distance from the vessel walls as the catheter 10 is situated within the narrow tortuous passageway. Alternatively, a plurality of standoff balloons may be used. Balloon 27 is inflated and deflated through the use of a lumen 22 which is provided with a balloon inflation port 23. Both balloon inflation ports 21 and 23 are connected to a suitable known means,for inflating and deflating the respective balloons. For clarity purposes, the lumens 20 and 22 are not shown extending throughout the length of the treatment lumen 25, these lumens however are connected to their respective balloons 18 and 27. The proximal end 15 of the treatment lumen 25 is connected to a relatively long transport tube 24 which allows radiation source 19 to be maneuvered to the site of treatment.

Figure 2:
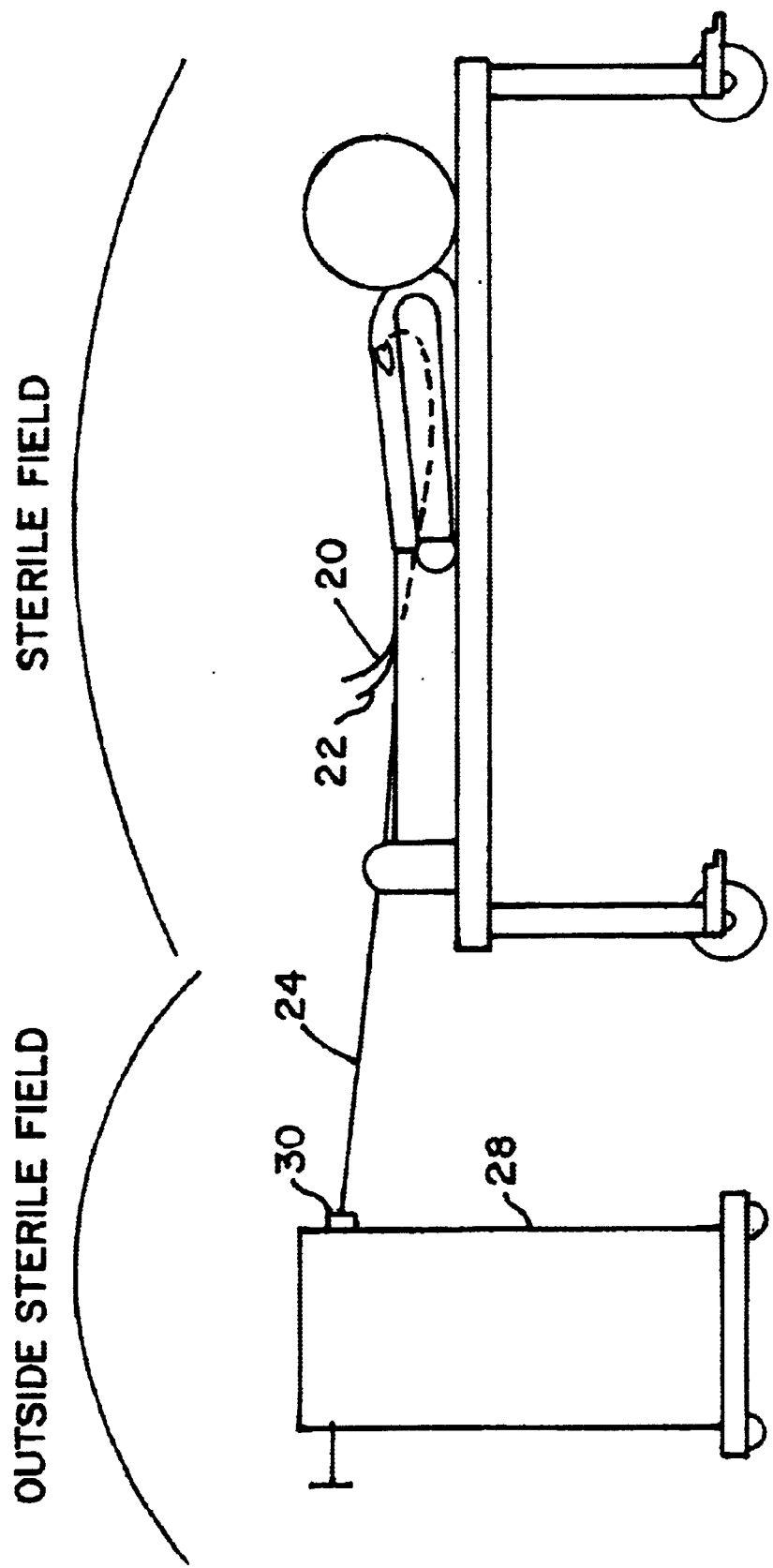
FIG. 2 is a side schematic view of a patient being treated with a catheter system according to the present disclosure.

A specially shaped connector hub 26 is used to connect the transport tube 24 to a connector port 30 of an afterloader device 28, as schematically shown in FIG. 2. It is important to note that most of the length of the transport tube 24 could be included outside the sterile field. The section of the transport tube 24 located outside the sterile field facilitates transportation of the radiation source 19 from the afterloader 28 to the site of the stenosis or other treatment through the transport tube 24 and the treatment lumen 25.

FIGS. 3 through 6 illustrate the connection between hub 26 and connector port 30 in greater detail. The transport tube 24 is provided with an inner wall 32 which tapers inwardly from a funnel opening 34 to facilitate introduction of the radioactive source or sources into the transport tube 24.

The connector port 30 includes a socket portion to receive the transport tube 24 therein. Mechanical switches 50 and 52 are provided with respective pressure sensing devices which may be in the form of plungers 46 and 48 located inside the connector port 30 of the remote afterloader. The switches 50 and 52, which may be any suitable known devices, are in direct communication with various electronic devices associated with the remote afterloader which determine whether or not the transport tube 24 is positively affixed to the connector port 30. This information is relayed to the control devices of the remote afterloader through wiring 54. Alternatively, non-hard wired communications methods can be used.

Figure 3:
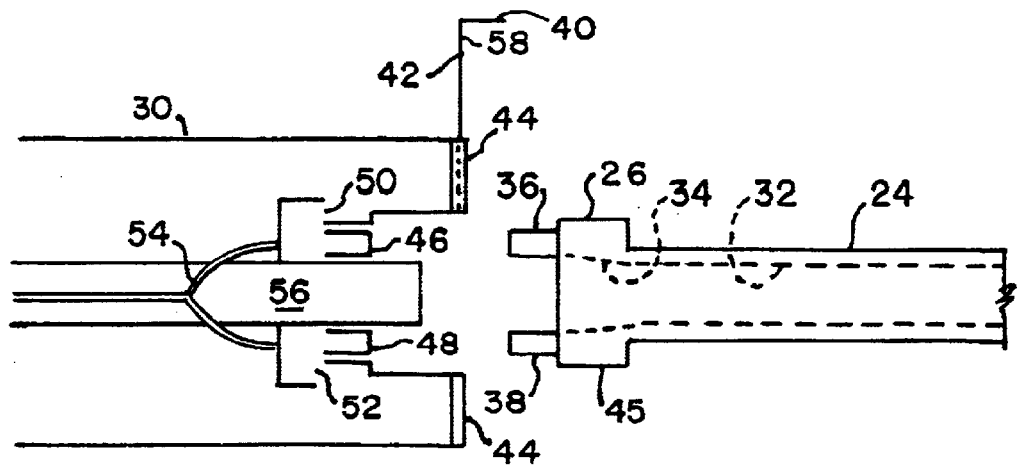
FIG. 3 is a partial side view of a treatment lumen and hub prior to being connected to a connector port of the presently disclosed afterloader unit.

The proximal end of the hub 26 is provided with two extension members 36 and 38. As shown in FIGS. 1A and 1B these members 36 and 38 may be of different lengths. Alternatively, members 36 and 38 may be of even length, as shown in FIG. 3. Further, hub 26 is shown to be of round geometry. However, it is within the scope of the present disclosure that hub 26 may be of any suitable geometry and connector port 30 may be of any suitable complementary geometry such that the two mate properly. When the transport tube 24 is positively mated to the connector port 30 of the afterloader, extension member 36 contacts a sensor 46 and extension member 38 contacts a sensor 48.

Sensors 46 and 48 may be any suitable sensing device which senses the presence or proximity of extension members 36 and 38. For example, sensors 46 and 48 may be mechanical plunger type devices or they may be any suitable known optical sensors. In such an embodiment, the optical sensor would likely be arranged such that the sensor is directed transverse to the distal end portion of connector port 30 such that the sensor would detect when the proximal end of hub 26 was in correct proximity to connector port 30.

Based upon the particular construction of the afterloader and the transport tube 24, the remote afterloader would not allow the radioactive source or sources to pass through a conduit 56 within the afterloader or to enter the interior of the transport tube 24 unless one or both of the sensors 46, 48 are in direct contact with their respective extension members 36, 38.

Figure 4:
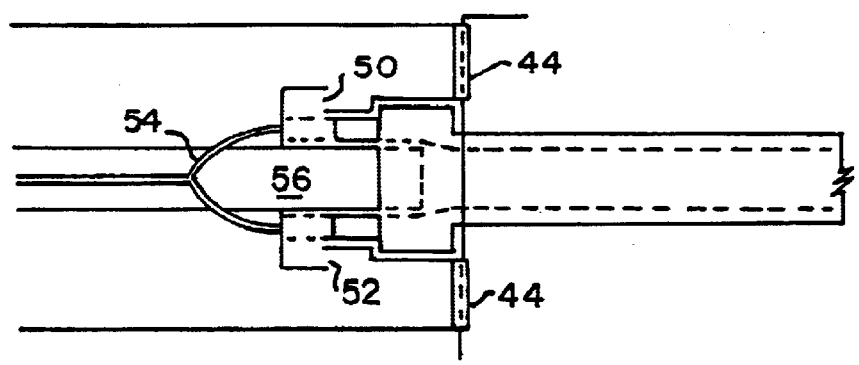
FIG. 4 is a partial side view, similar to FIG. 3, which shows a treatment lumen positioned and locked to the connector port of the afterloader unit.

Referring to FIG. 4, the connection between the transport tube 24 and the remote afterloader will now be described in detail. When either of the sensors 46 or 48 or both are depressed and the transport tube 24 is locked firmly to the afterloader by a slide plate 42, an opening is provided which is too small to allow the extended portion 45 of the hub 26 of the transport tube 24 to pull through. Since one or more of the pressure sensors 46, 48 is depressed, a signal is sent to the controller electronics to allow movement of a drive member through the conduit 56 to allow one or more of the radioactive sources 19 to pass into the transport tube 24.

Figure 5:
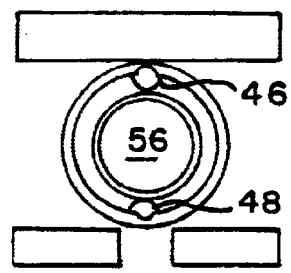
FIG. 5 is a frontal view of the connector port of the afterloader unit without a catheter connected thereto.
Figure 6:
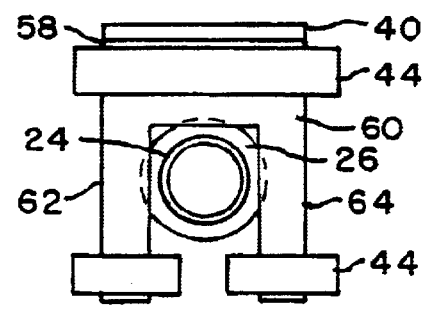
FIG. 6 is a frontal cut-away view of the hub and catheter after being locked in place to the connector port of the remote afterloader unit.

FIGS. 5 and 6 further illustrate the locking device as described in connection with FIG. 4 as firmly holding the transport tube 24 in the locked position. The locking device includes the sliding plate 58 fitting into horizontal guiding channels 44, located adjacent to the exit port of the remote afterloader. The sliding plate 58 includes a lip 40 for proper seating in the top horizontal guiding channel 44. The sliding plate 58 can contain an opening large enough to allow the tubing section of the transport tube 24 to pass, but not the hub 26 of the tube, or it can bite or grip on the wall of the tubing section of the transport tube 24. This opening is created by providing two vertical portions 62, 64 connected to a horizontal portion 60.

It is noted that other locking mechanisms could be utilized. For example, a rotating plate could be used which defines an opening large enough to allow the tubing section of the transport tube 24 to pass, but not the hub 26 of the tube. Alternatively, the plate could bite or grip on to the wall of the tubing section of the transport tube 24.

In operation, the flexible guidewire 12 is inserted into the body through a small incision and is then introduced into a blood vessel or similar conduit or passageway and is maneuvered to the treatment site. The catheter 10 is then threaded over the guidewire 12 and is also advanced to the location of treatment. At this point the dilatation balloon or balloons is inflated and deflated one or more times to reduce the size of the stenosis.

If a standoff balloon or balloons are provided, it is inflated at this point. These standoff balloons inflate so as to maintain the treatment lumen of the catheter at a predetermined standoff distance from the vessel wall inside the prior stenosised area while allowing for maximum bodily perfusion. The hub 26 connected to the elongated transport tube 24 is attached to the connection port 30 of the afterloader. Assuming the transport tube 24 is properly connected to the afterloader, one or more of the radioactive sources is maneuvered through conduit 56 of the afterloader to the transport tube 24 and then to the site of treatment.

After a predetermined period of time has elapsed, the standoff balloon or balloons are deflated and the radioactive source or sources as well as the catheter and the guidewire are removed from the bodily conduit or passageway.

Although the present disclosure has been described with reference to specific details of certain embodiments thereof, it is not intended that such details should be regarded as limitations upon the scope of the disclosure except as and to the extent that they are included in the accompanying claims.

What is claimed is:

1. A system for delivering a medical treatment to a treatment site in a vessel or other conduit in a mammalian body, which comprises:

an afterloader including a housing, a drive member, and a conduit having a first end operatively associated with an output portion of the drive member, and a connector disposed at a second end, the connector defining a first mating surface;

an elongated transport tube having a proximal end defining a second mating surface, the first and second mating surfaces being complementarily configured and dimensioned such that a continuous passageway is formed between the conduit and the elongated transport tube;

a locking member positionable within a channel formed adjacent either the first or second mating surfaces and being configured and dimensioned such that upon insertion of the locking member in the channel the first and second mating surfaces are securely mated.

2. The system in accordance with claim 1, wherein the second mating surface includes at least one extended portion.

3. The system in accordance with claim 2, wherein the first mating surface includes a presence sensing mechanism having an actuator aligned and operatively interactive with the at least one extended portion of the second mating surface.

4. The system in accordance with claim 1, wherein the transport tube includes a hub portion formed at a proximal end thereof.

5. The system in accordance with claim 4, wherein the channel is formed adjacent the first mating surface such that upon insertion of the locking member in the channel, the hub portion of the transport tube is retained by the locking member.

6. The system in accordance with claim 1, which further comprises a presence sensing mechanism operatively interactive with the second mating surface such that upon substantially complete mating between the first and second mating surfaces a signal is provided to the user at a remote location that the connection has been made.

7. The system in accordance with claim 1, wherein the locking member is a plate having defining an opening at least as large as the continuous passageway and smaller than an outer dimension of the transport tube such that upon insertion of the locking member in the channel the transport tube is securely connected to the afterloader.

8. The system in accordance with claim 1, wherein the proximal end of the treatment tube defines a tapered opening.

9. A system for delivering a medical treatment to a treatment-site in a vessel or other conduit in a mammalian body, which comprises:

an afterloader including a housing, a drive member, and a conduit having a first end operatively associated with an output portion of the drive member, and a connector disposed at a second end, the connector defining a first mating surface having a presence sensing mechanism disposed thereon; and an elongated transport tube having a proximal end defining a second mating surface, the first and second mating surfaces being complementarily configured and dimensioned such that a continuous passageway is formed between the conduit and the elongated transport tube and further upon substantially complete mating of the first and second mating surfaces, the presence sensing mechanism provides an indication of the connection.

10. A system according to claim 9, wherein the presence sensing mechanism is a mechanical switch.

11. A system according to claim 10, wherein the mechanical switch includes a pressure sensitive actuator operatively interactive with the second mating surface.

12. A system in accordance with claim 11, wherein the second mating surface includes an extended portion aligned with the actuator.

13. A system according to claim 9, wherein the presence sensing mechanism includes an optical sensor 14.

14. The system in accordance with claim 9, wherein the first mating surface defines a socket and the transport tube includes a hub portion formed at a proximal end, such that the hub portion is receivable in the socket and is releasably retainable therein.

15. The system in accordance with claim 14, which further comprises a locking member defining an opening smaller than an outer dimension of the hub portion, the locking member engageable with the distal end of the connector to retain the hub within the socket.

16. A device for treating an occlusion or constriction in a vessel or other bodily conduit, which comprises:

an elongated flexible catheter having a proximal end and a distal end;

a balloon system disposed about the catheter near the distal end thereof;

a conduit extending along the catheter from the proximal end thereof to at least a position adjacent the balloon system; and a hollow treatment lumen disposed within the catheter and defining an interior chamber sealed from fluid communication with the exterior of the lumen, the treatment lumen having a proximal portion which defines an elongated extension such that a medical treatment source is maneuverable from a non-sterile environment disposed a distance away from an treatment site to a sterile field disposed in proximity to the treatment site.

17. A device according to claim 16, wherein the balloon system is a dilatation balloon.

18. A device according to claim 16, wherein the balloon system is a stand-off balloon which upon inflation, maintains the treatment lumen at a predetermined spacing from an interior wall of the vessel.

19. A method of delivering a medical treatment to a treatment site in a vessel or other conduit in a mammalian body, comprising the steps of:

providing an afterloader including a housing, a drive member, and a conduit having a first end operatively associated with an output portion of the drive member, and a connector disposed at a second end, the connector defining a first mating surface having a presence sensing mechanism disposed thereon; and connecting an elongated transport tube having a proximal end defining a second mating surface to form a continuous passageway between the conduit and the elongated transport tube;

locking the first and second mating surfaces together with a locking mechanism including a plate member positionable within a channel formed on one of the mating surfaces;

sensing a substantially complete connection between the first and second mating surfaces; and advancing a medical treatment source through the transport tube to a treatment site.

20. The method according to claim 19, wherein the step of advancing a medical treatment includes advancing a radiation source through the transport tube.

21. The method according to claim 20, wherein the step of advancing a medical treatment further includes, advancing the radiation source through the transport tube wherein the radiation source is attached to a source wire fed through the transport tube.

* * * * *